United States Patent [19]

Kolobanov et al.

[11] Patent Number: 4,973,848
[45] Date of Patent: Nov. 27, 1990

[54] LASER APPARATUS FOR CONCURRENT ANALYSIS AND TREATMENT

[75] Inventors: Alexander S. Kolobanov; Rostislav D. Barabash, both of Moscow, U.S.S.R.

[73] Assignee: J. McCaughan, Columbus, Ohio

[21] Appl. No.: 388,983

[22] Filed: Jul. 28, 1989

[51] Int. Cl.[5] ............................................. G01N 21/64
[52] U.S. Cl. ............................... 250/458.1; 250/461.1; 250/461.2
[58] Field of Search ............... 250/461.2, 461.1, 458.1; 128/634, 633, 665

[56] References Cited

U.S. PATENT DOCUMENTS

| | | | |
|---|---|---|---|
| 3,757,250 | 9/1973 | Packard et al. | 372/43 |
| 4,316,467 | 2/1982 | Muckerheide | 606/9 |
| 4,576,173 | 3/1986 | Parker et al. | 128/633 |
| 4,660,925 | 4/1987 | McCaughan, Jr. | 350/96.15 |
| 4,693,556 | 9/1987 | McCaughan, Jr. | 350/320 |
| 4,718,417 | 1/1988 | Kittrell et al. | 606/7 |
| 4,733,660 | 3/1988 | Itzkan | 606/9 |
| 4,768,513 | 9/1988 | Suzuki | 128/634 |
| 4,852,579 | 8/1989 | Gilstad et al. | 128/665 |

OTHER PUBLICATIONS

Cutruzzola et al., "Change in Laser-Induced Arterial Fluorescence During Ablation of Atherosclerotic placque." *Lasers in Surgery and Medicine* 9:109–117 (1989).
Sroka et al., "Comparison of Fluorescing and Photosensitizing Properties of Different Porphyrin-Derivative Preparations," in *Light in Biology and Medicine, vol. 1.* Douglas et al., eds. (Plenum Publishing Corp., New York, 1988), pp. 127–132.
Dougherty et al., "The Structure of the Active Component of Hematoporphyrin Derivative," in *Porphyrin Localization and Treatment of Tumors,* Doiron et al., eds. (Alan R. Liss, Inc, New York, 1984), pp. 301–314.
McCaughan, Jr. et al., "Hematoporphyrin-Derivative and Photoradiation Therapy of Malignant Tumors." *Lasers in Surgery and Medicine* 3: 199–209 (1983).
Cortese et al., "Endoscopic Management of Lung Cancer with Hematoporphyrin Derivative Phototherapy." *Mayo Clinic Proceedings* 57:543–547 (1982).
King et al., "Fluorescence Bronchoscopy in the Localization of Bronchogenic Carcinoma." *Cancer* 49:777–782 (1982).
Doiron et al., "Fluorescence Bronchoscopy for Detection of Lung Cancer," *Chest* 76:27–32 (1979).

Primary Examiner—Constantine Hannaher
Attorney, Agent, or Firm—G. Wolken, Jr.

[57] ABSTRACT

The present invention discloses an apparatus in which two laser beams are concurrently scanned across a region of tissue to be treated by laser therapy. A first "analysis" beam is used to excite characteristic light emission or reflection from the surface. This scattered light is detected and analyzed to determine the properties of the small portion of the surface under illumination and at that instant by the analysis beam. A second "treatment" beam is scanned concurrently with the analysis beam. The properties of the surface at each small region (as determined by the analysis beam) are used to adjust the power and other properties of the treatment beam such that each small region of the surface receives optimal exposure. Automatic controlled scanning of both beams allows very rapid treatment of large areas of tissue, while adjusting in real-time the power levels of the lasers to achieve optimal treatment at each point treated.

8 Claims, 3 Drawing Sheets

LASER APPARATUS FOR CONCURRENT ANALYSIS AND TREATMENT

BACKGROUND OF INVENTION

1. Field of Invention

This invention relates to a device for scanning, detecting and controlling directed beams of laser light, and more particularly to a device for scanning concurrently two beams of laser light across an area to be treated by one of said light beams (the "treating beam") while the second of said beams (the "analysis beam") detects the properties of the scanned area and controls the intensity and certain other properties of the treating beam so as to provide continuous optimal treatment despite variations in the properties of the scanned area.

2. Summary of Technical Background

There are at least three characteristics of laser light which have led to the increasing importance of lasers in science, engineering and medicine. These characteristics are: (1) Lasers typically produce light having a very precise wavelength. Thus, such light is capable of exciting very well-defined atomic and molecular transitions in specific substances, leading to the possibility of accurate detection and analysis. (2) Monochromatic and coherent laser light is capable of being focused to a very small spot. This leads to the possibility of accurate spacia resolution. (3) Laser light can be produced in focused or diffuse spots with considerable power density, thus leading to the possibility of beneficial processing of the target substance solely by means of laser light.

The invention described herein uses all three characteristics of laser light. In order to be concrete, our discussion will emphasize the problems associated with lasers as tools for medical diagnosis and treatment. However, the invention described herein is simply adaptable to any problem requiring a continuous analysis and laser treatment of a region with nonuniform characteristics. Such problems may occur in laser processing of metals, alloys, ceramics, plastics or other materials in which, due to prior processing or inherent properties, the optimal laser processing parameters vary over the region. The modification of the apparatus described herein to handle such nonmedical problems would be obvious to anyone having ordinary skills.

Lasers in medicine have been used in many applications, both with relatively low powers of laser light as a diagnostic technique, and with relatively high powers as a method of treatment. For example, in general surgery lasers have been used for the cutting of tissues, selective biostimulation and coagulation of bleeding, nonhealing and suppurative wounds and ulcers. In physiotherapy lasers have been used for irradiation of inflamed areas of skin, mucosa, joints, reflexogenic zones and acupuncture points. Typically in such applications treatment is usually performed by a helium-neon ("He-Ne") laser (emitting light with a wavelength of typically 633 nanometers, "nm") or with a diode laser (emitting typically in the region 800 to 900 nm). Typically, He-Ne lasers are used in such applications to deliver power in the range 1–30 milliwatts ("mW"), while the diode lasers will typically be used to deliver 1–5 mW. Treatment is typically performed by delivery of the light either through flexible optical fibers or by manipulation of mirrors. When stimulating the regeneration of large, injured inflamed areas or stimulating the response from reflexogenic zones, the laser beam is typically dispersed by means of a lens having a relatively short focal length to cover the whole (or at least an expanded region) of the target area requiring treatment. Typically, the targets treated by this method will be from 1 to 15 cm in diameter and require 0.1 to 3.0 mW/(cm$^2$) of laser power delivered to the target. Diode lasers are occasionally used in a modulated mode depending on the treatment purposes.

A common problem in the treatments described above is the need to treat an area with laser light in which, typically, different parts of the total area to be treated will require different levels of exposure to laser light. The consequences of overexposure may be very severe (as in the removal of arterial plaque described below), or not serious enough to cause concern. The problem addressed by the present invention is to regulate and to deliver the therapeutic dosage of laser light to every point requiring treatment, while reducing overexposure of any area.

Lasers have also been used in dermatology and cosmetology for photothermal evaporation or photochemical decolorization of portwine stains, birthmarks, freckles, tattoos, etc. The photothermal evaporation and photochemical decolorization of hyperpigmented areas are typically performed by means of a carbon dioxide laser (emitting typically at a wavelength near 10,600 nm), or an argon laser (emitting typically 488 nm and 514 nm). Treatment powers typically in the range 3–50 watts ("W") are employed using either a fiber optical beam delivery or a system of hard mirrors depending on the characteristics of the laser (that is, the ability of present optical fibers to transmit that wavelength light at the required power level).

Carbon dioxide and argon lasers are also typically used for the cauterization of bleeding capillaries and larger blood vessels, and to coagulate suppurative and necrotic tissues of abscesses, wounds, or ulcers, and for evaporation and decolorization. For such applications, the distal tip of the light delivery system is typically moved by the surgeon by hand in an attempt to irradiate uniformly all points of the pathological area. In such procedures, typically the distance between the distal tip of the light delivery system is varied by the surgeon to adjust the power density (W/cm$^2$) delivered to the pathological area. The length of time the surgeon exposes each area, multiplied by the delivered power density, determines the total exposure to light, measured typically in Joules ("J")/(cm$^2$). The experience and intuition of the surgeon determines the exposure delivered at each point of the region, which can easily result in under- or overexposures for even the most expert surgeons. It is a major purpose of the present invention to provide the surgeon with more quantitative data about the region to be treated and, in appropriate cases, to automate the scanning, analysis and treatment procedures.

A very important new application for laser surgery is in the field of cardiology, removing arterial obstructions by means of laser light delivered through an optical fiber. The use of laser surgery in this manner removes the need to open the chest and interrupt blood flow for the duration of the surgical procedure (an advantage, also, in surgery in the abdomen and other body cavities). A major impediment to full clinical application of such surgery is the possibility that the surgeon will not be able to tell obstructing plaque from the wall of the blood vessel itself. Thus, inadvertent puncture of the wall of a major blood vessel is very possible:

a very serious problem as the vessel is not immediately accessible to the surgeon for repair.

A recent advance in this area has been the work of F. W. Cutruzzola et. al. ("Change in Laser-Induced Arterial Fluorescence During Ablation of Atherosclerotic Plaque", *Lasers Surg. Med.* Vol 9, No. 2, pp. 109–116, 1989). In this work on human cadaver aorta, it was found that laser-induced florescence spectroscopy is capable of discriminating atherosclerotic regions from normal aorta. Thus, the possibility is present to let the surgeon analyze "on the fly" the region of aorta to be laser-ablated just prior to such ablation. Equally important, continuous analysis by laser spectroscopy will tell the surgeon when ablation has proceeded far enough, and only normal aorta remains. This is the surgeon's signal that no further ablation of that particular region is needed and attention should be turned elsewhere before puncture of the aorta wall occurs. Extensive use of this technique has been demonstrated by Kittrell et al in U.S. Pat. No. 4,718,417.

Thus, for the removal of aorta plaque it has been demonstrated that laser analysis of the region to be treated, as well as laser treatment may both be necessary for effective surgery. The invention described herein consists of apparatus for assisting the laser surgeon in performing such analysis and treatments in a variety of surgical and medical applications.

The invention described herein relates to an apparatus for the automatic adjustment of power and properties the treating laser beam in accordance with information obtained by means of a probe or analyzing laser beam. (Fully automated scanning is an optional feature of the invention, appropriate for some applications, but not required for those cases in which the surgeon desires to maintain manual control.) As such, it will have obvious applications to those areas of medicine and surgery described above, and others which will be obvious to practitioners having ordinary skills in those fields. However, a major impetus for the development of this invention is for the photodynamic treatment of cancer. Such photodynamic therapy ("PDT") procedures will be the focus of our discussion and supply the primary examples for the uses of the invention described herein. Such emphasis on PDT is in no way intended to exclude other applications as discussed above.

PDT is based upon the existence of certain chemicals which are selectively retained (or conceivably, selectively absorbed) by cancer cells. It is also known that some of these selectively-retained chemicals cause destruction of the cells in which they reside when exposed to light of sufficient intensity and having the appropriate wavelength. Such selective photosensitization is becoming an accepted cancer treatment in appropriate situations.

The leading photochemical cancer treatment at this time involves the injection into the patient of a hematoporphyrin derivative ("HpD"). This drug permeates the tissues of the patient, but typically dissipates from normal cells in 24–48 hours. HpD is typically retained for a longer time by cancer cells. When exposed to light of sufficient intensity and at the appropriate wavelength, HpD undergoes a chemical reaction leading to the destruction of the cell in which it resides. Thus, appropriate timing of the exposure of the patient to light following the administration of HpD leads to selective destruction of those cancer cells exposed to said light. It is generally thought that the mechanism of photochemical cell death involves the production of the singlet electronic state of molecular oxygen, which attacks vital portions of the cell.

However, it is necessary to exercise care in the exposure of the patient to light following HpD administration. Overexposure of the patient can lead to the unwanted death of normal cells (presumably containing trace amounts of HpD at the time of treatment with light). Underexposure will lead to incomplete destruction of the patients cancer cells, obviously leading to a recurrence of the disease. Thus, surgeons would very much like to be able to monitor the dosage delivered to each point of the affected region and, at the same time, monitor the concentration of photosensitizing chemical (typically, HpD).

Other photosensitizers are currently in various stages of development, experimental and clinical use. These include psoralens, fluorescein, rose bengal, rhodamine 123, various modifications to HpD, Photosan (the tradename of Seehof Laboratory, Federal Republic of Germany), Photofrin (the tradename of QLT Phototherapeutics, Inc., Vancouver, British Columbia, Canada), pheophoride, chlorins, purpurins, phthalocyanines, naphthalocynanines, and others for purposes of diagnosis (typically by fluorescence of the drug) and for photodynamic treatment in the manner of PDT described above.

The choice of necessary laser power and wavelength typically depends upon the extent to which the light beam in question penetrates the natural tissue, by the absorption and fluorescence spectra of the natural pigments and artificial photosensitizers.

For the case of PDT performed with HpD photosentizer, much work has been done on light-induced fluorescence as a means to detect the locations of HpD prior to treatment. Typical (non-laser) excitation is performed by means of a (typically) 200 W mercury lamp, filtered to provide a relatively narrow emission peak near 405 nm. (For example, see D. R. Doiron et. al., "Fluorescence Bronchoscopy for Detection of Lung Cancer", *Chest*, Vol. 76, PP. 27–32, July 1979). Laser light may also be used, for example a Spectra-Physics Model 164-11/265 ® krypton ion laser, capable of emitting 200 mW of power in three closely spaced lines in the violet region of the visible spectrum (406 nm–415 nm). The laser beam is typically focused by a lens onto the core of a suitable optical fiber, typically a nonfluorescing fused quartz fiber with a core approximately 0.40 mm in diameter. (See, for example, E. G. King et. al. "Fluorescence Bronchoscopy in the Localization of Bronchogenic Carcinoma", *Cancer*, Vol. 49, pp. 777–782, 1982). The resulting red fluorescence is typically collected by means of the objective lens of an endoscope and focused on the photocathode of an image intensifier. Typically, on the way to the image intensifier tube the light is processed by passing through a nonfluorescent red bandpass filter designed to reject the reflected violet light from the exciting laser, as well as to reject most of the fluorescence from normal tissue. In a typical application, the image intensifier consists of a three-stage, electrostatic-focus tube with an overall gain more than 30,000. Thus, a dim red image passing through the endoscope is transformed into a bright green image which can be viewed by the medical team and photographed at the output of the intensifier. A significant disadvantage of this method is the need for continuous adjustment by hand of the endoscopic fiber (or other means employed to deliver the analyzing light) to compensate for movement in the irradiated area. Such movements would typically be most pronounced in the study of contracting or pulsating organs such as the stomach.

Such fluorescence serves as a means to locate the photosensitizers and, hence, locate the diseased cells to be treated. This technique has been in use long before it was realized that light could also serve as the method of treatment, simply using the fluorescence as a means for locating the region for conventional surgical removal. However, the treatment possibilities have expanded considerably with the realization that intense light (typically having a different wavelength from the fluorescence-inducing, or analysis, light) could also lead to the destruction of the diseased cells. For the example of HpD, it is believed that this destruction proceeds by means of the production of singlet oxygen.

The use of a second light source (typically a laser) as the method of treatment is quickly becoming an important medical procedure. HpD has been approved for clinical trials for the in situ production of singlet oxygen and the local destruction of tissues and malignant tumors. (For example, see the work of J. S. McCaughan et. al., "Hematoporphyrin-Derivative and Photoradiation Therapy of Malignant Tumors", *Lasers Surg. Med.*, Vol. 3, pp. 199–209, 1983, and the review article by T. J. Dougherty et. al. "The Structure of the Active Component of Hematoporphyrin Derivative", in *Porphyrin Localization and Treatment of Tumors*, Eds. D. R. Doiron and C. J. Gomer {Alan R. Liss, Inc., New York, 1984}, pp 301–314). Other photosensitizing drugs are also under very active investigation. For example, DHE/Photofrin has been the subject of a recent U.S. Patent (T. J. Dougherty et. al., U.S. Pat. No. 4,649,151), while photosan has been the subject of recent publications (for example see the review article of R. Sroka et. al. "Comparison of Fluorescing and Photosensitizing Properties of Different Porphyrin-Derivative Preparations", appearing in *Light in Biology and Medicine*, Vol. 1, R. H. Douglas et. al., eds. {Plenum Publishing Corp., New York, 1988}, pp. 127–132).

The production and delivery of the light necessary to produce singlet oxygen and to destroy the tumor is still the subject of active research. It is important in the choice of a light source to achieve a balance of three considerations. First, it is necessary to use light having a wavelength producing sufficient singlet oxygen to effectively kill the tumor cell. However, the wavelength most effective in cell destruction may not penetrate to the site of the tumor very well. Therefore, the second consideration to be taken into account is to use a wavelength that penetrates through typical tissues and reaches the tumor to be treated with sufficient intensity to have the desired therapeutic results. The third consideration is that there must be available a suitably intense source of light at the desired wavelength to deliver therapeutic intensities to the tumor site. A balance of these three considerations must be obtained to achieve effective medical treatment. For HpD, it is typical to use a wavelength of 630 nm. While this is not the most efficient wavelength for causing the production of singlet oxygen, it efficiently penetrates typical biological tissues.

A commonly used method to produce 630 nm light is to employ the continuous wave ("cw") radiation from an argon laser as the pumping device to pump a dye laser. In typical operation, the argon laser will be used to emit radiation at 488 nm or 514 nm pumping a dye laser (typically Rhodamine B or similar dye) adjusted to emit cw radiation at 630 nm (in the red region of the visible spectrum). An alternative method is to use the pulsed output from a gold vapor laser at a wavelength of 628 nm or copper vapor laser at 511 nm or 578 nm to pump a similar dye laser, similarly adjusted to emit at the wavelength of 630 nm. Occasionally, two-photon excitation of such dyes is obtained by pumping with a Nd:YAG laser.

Other photosensitizers currently under investigation (such as vitamin B12, riboflavin, or the psoralens) are used in conjunction with excitation by means of light from the ultraviolet region of the spectrum. Tetracycline, acriflavine, stilbene 420 are examples of photosensitizers using excitation by blue light. Green/yellow light is typically employed to excite fluorescein or rose bengal photosensitizers, while dark red, and infrared light is commonly used in conjunction with methylene blue, pheophorbide, chlorins, lacteriochlorins purpurins, the phthalocyanines, or the naphthalocynanines photosensitizers. In all of these cases both laser and noncoherent (nonlaser) light sources have been used. However, it is typically much more difficult to achieve therapeutic light intensities at the tumor site if lasers are not used. These difficulties are increased if it is required that the light be delivered to the tumor site through an optical fiber, in which coupling nonlaser light into the fiber core requires focusing to a fine spot.

We wish to draw two conclusions from this summary. First, even for a relatively standard PDT procedure, (HpD excited at 630 nm), there is still room for an improved source of light. Second, many novel photosensitizers are under active development. For each such photosentizer a different optimal light source will generally be required. It will introduce major roadblocks to full medical application if a different light source must be engineered for each photosentizer.

It is an important component of the present invention to introduce a flexible laser system, capable of rapid modification to produce light at numerous different frequencies. The light source of the present invention also has certain advantages in the excitation of HpD at 630 nm. The present system can be based, as one of several possible embodiments, upon electron-beam pumping of a semiconductor laser as, for example, disclosed for TV-imaging purposes in the patent of J. R. Packard et. al. (U.S. Pat. No. 3,757,250, {1973}), described in more detail below.

An important advantage of PDT is the possibility of delivering therapeutic intensities of light to the site of the tumor through a flexible, thin optical fiber. In many cases, this can eliminate the need for major surgery in treating tumors in locations which can be reached through body orifices (such as lung, esophagus, stomach, bladder, colon, rectum, etc). In many other cases, such as brain tumors, the treating light can be delivered by means of a fiber inserted into the tumor through a thin needle, markedly reducing damage to intervening, non-tumorous, tissues which conventional surgery would entail. However, the use of optical fibers requires the surgeon to consider the best way to achieve a uniform cell-killing dosage of light throughout the tumorous region. This must be accomplished in spite of varying tumor extents and depths. Clearly, not killing all cancerous tumor cells will lead to the recurrence of the tumor. However, overexposure of non-tumor cells (in which unavoidable traces of photosentizer will be present), should also be avoided. Simply "flooding" the region of the tumor with excessive amounts of light should be avoided as this can lead to the destruction of non-tumorous cells. In certain locations, such as arterial walls, the resulting punctures could be life-threatening for the patient. In other applications, prudent medical procedure will strive to minimize the destruction of non-cancerous cells. This problem is also the subject of the present invention. To more fully describe the advantages of the present invention, we will first describe some of the procedures of PDT performed through an optical fiber.

For the most widespread therapeutic combination of HpD (Photofrin) in combination with an argon pumped dye laser, a typical optical fiber would be a medical-grade quartz fiber having a core diameter of, typically, 0.4 mm. The light exiting from the optical fiber is typically in the approximate shape of a cone with, typically, a divergence about 20 deg. The fiber is typically passed through the open channel of a flexible endoscope such that the distal end protrudes from the tip of the endoscope. A small microlens may be attached integrally to the distal tip of the fiber. In this way the emerging light can be dispersed over a typical diameter of 10 to 12 mm when the fiber is held 1.0 to 1.5 cm from the surface of the tumor, and still produce sufficient intensity over the dispersed region. The proximal end of the fiber is typically attached to a positioning device, or manually manipulated by the surgeon.

The light from the 630 nm source is typically focused directly onto the proximal end of the optical fiber. Typically the light source consists of an argon-pumped dye laser in which the dye (typically Rhodamine B) is circulated through the resonator cavity to avoid a gradual loss over time of laser power emitted at 630 nm. An argon laser with a typical maximum cw power of 20 W is capable of producing an output of 4 W of 630 nm light from a typical dye laser. The output power delivered by the optical fiber is typically measured by means of an externally-calibrated, continuous-wave power meter (as described more fully by D. A. Cortese and J. H. Kinsey, "Endoscopic Management of Lung Cancer with Hematoporphyrin Derivative Phototherapy", *Mayo Clinic Proceedings*, Vol. 57, pp. 543–547, Sept. 1982).

As discussed above, it is important for the surgeon to be able to deliver a known dose to each point of the tumor. Since such endoscopic procedures are frequently done under general anaesthetic, it is also important to minimize the time of treatment. This has led to the development of modifications of the distal tip of the delivery optical fiber to produce more useful patters of light emitted from the end of the fiber. For example, the patents issued to J. H. McCaughan (U.S. Pat. Nos. 4,660,925 {1987}, and 4,693,556 {1987}) describe devices constructed on the distal end of optical fibers such that the emitted light emerges in uniform cylindrical or spherical patterns, respectively. Such devices have proven themselves to be particularly in obtaining uniform irradiation of tumors of different shapes and extent localized in the bladder, cervix, esophagus, stomach, lung and other more-or-less cylindrical or spherical cavities. The clear limitations of such devices are that not all such tumors have precise cylindrical or spherical symmetry. Thus, it is very difficult to achieve selective irradiation of such tumors having other than precise cylindrical or spherical shapes without simultaneous radiation of residual photosensitizer in adjacent, non-cancerous tissues. Constructing a stencil to shield all but the region of the tumor is one possible solution, but suffers from the disadvantages of requiring prior knowledge of the precise shape of the tumor and must be held in position by the surgeon during the procedure. Both requirements add to the total time of the procedure which must be endured by the patient.

Realistic tumors occurring in patients lack a well-defined geometrical shape, making uniform irradiation of the entire tumor very difficult. A further complication is that, even in regions generally considered "tumor" there will be varying concentrations of photosensitizer. For instance, tumors having different depths of cancerous cells (not uncommon) will appear to the surgeon to have different concentrations of photosensitizer. Thicker tumors will naturally require exposure to more therapeutic light to penetrate and destroy the underlying tumor layers. These complications are virtually impossible to be handled by visual inspection, even by very experienced surgeons. Therefore, it is very important to develop ways in which the surgeon can analyze "on-the-fly" at point to point across the tumor the concentration of photosensitizer and, therefore, the amount of light exposure required for full, yet not overexposed, therapeutic treatment.

One approach to this problem of in situ analysis of the concentration of photosensitizer in and around tumors, is that recently patented by J. G. Parker et. al. (U.S. Pat. No. 4,576,173 {1986}). In this work it was recognized that the effective agent in the destruction of cells is the production of singlet oxygen. Thus, this invention discloses a method for monitoring directly the concentration of singlet oxygen. This is complicated by the fact that singlet oxygen emits in the midst of a broad band of background fluorescence from the surrounding medium. Nevertheless, this patent discloses a method involving chopping of the exciting radiation combined with phase sensitive detection to extract the singlet oxygen signal from the background.

The invention described herein consists of a method and apparatus of analysis for the photosensitizer itself rather than singlet oxygen. This offers the advantage simplified methods of detection to extract the signal from the background. In addition, the present invention describes a method for automatically scanning the treating laser beam (630 nm in the case of PDT using HpD). The present invention describes, in addition, a method for automatically controlling the power and certain other characteristics of the treating laser beam depending on the measured characteristics of the point to be treated as measured by the probe or analysis beam. The point-by-point adjustment of the treating laser beam can be used by the surgeon as an aid to his manual control of the surgeon. Alteratively, for appropriate tumors in suitable locations the fully automatic scanning mode can be employed with the treating laser beam being adjusted by the analysis beam without operator intervention in either beam adjustment or beam location.

SUMMARY AND OBJECTS OF THE INVENTION

The present invention discloses an apparatus in which two laser beams are concurrently scanned across a region to be treated. A first "analysis" beam is used to excite characteristic light emission or reflection from the surface, which light is detected at a location remote from said surface. Said detected light is analyzed to determine the properties of the small portion of the surface under illumination at that instant by the analysis beam. A second "treatment" beam is scanned concurrently with said analysis beam. The properties of the surface at each small region (as determined by the analysis beam) are used to adjust the power and other properties of said treatment beam such that each small region of the surface receives optimal processing by said treatment beam. Two alternative constructions of this apparatus are disclosed. In a first embodiment, the analysis beam and treatment beam are delivered to the surface in distinct optical paths. A second embodiment of the present invention disclosed herein has the analysis beam and treatment beam combined to follow a single optical path to the surface to be treated. The first two-path embodiment will be preferred, in general, in situations in which the analysis beam and treatment beam require different optical materials for efficient transmission and focusing. The second single-path embodiment will likely be the preferred embodiment when the same optics can transmit and focus both analysis and treatment beams. Both embodiments allow fully automated scanning and treatment in appropriate situations, as well as manual scanning, with or without light delivery through an optical fiber (or fibers). A method of treating cancerous tumors using photodynamic therapy in combination with the apparatus of the present invention is also disclosed.

Thus, a primary object of the present invention is to provide in combination a laser scanning and laser treatment in which the properties of the surface to be treated are analyzed by the analysis beam, and said properties are used in real-time to adjust the properties of the treatment beam to obtain optimal surface treatment at each point under investigation.

Another object of the present invention is to provide, via electron-beam-pumped semiconductor lasers, a flexible source of various wavelengths of laser light for various medical and surgical purposes.

Yet another object of the present invention is to provide apparatus for full automated scanning and treatment of a surface region, reducing the training and skill level required of the operator.

Another object of the present invention is to provide a laser surgeon an accurate analysis of the properties of the surface under treatment in time for said surgeon to make manual adjustments of the treatment parameters.

Another object of the present invention is to enhance the accuracy of light delivery in manual scanning by means of continuous analysis of the region undergoing treatment and continuous feedback to control the treatment laser.

DESCRIPTION OF PREFERRED EMBODIMENTS

There are embodiments of the present invention which would be preferred for different medical procedures. Here we will describe typical embodiments that would be useful in several different circumstances. Other modifications will readily be apparent to one with ordinary skills in the field.

Figure 1:
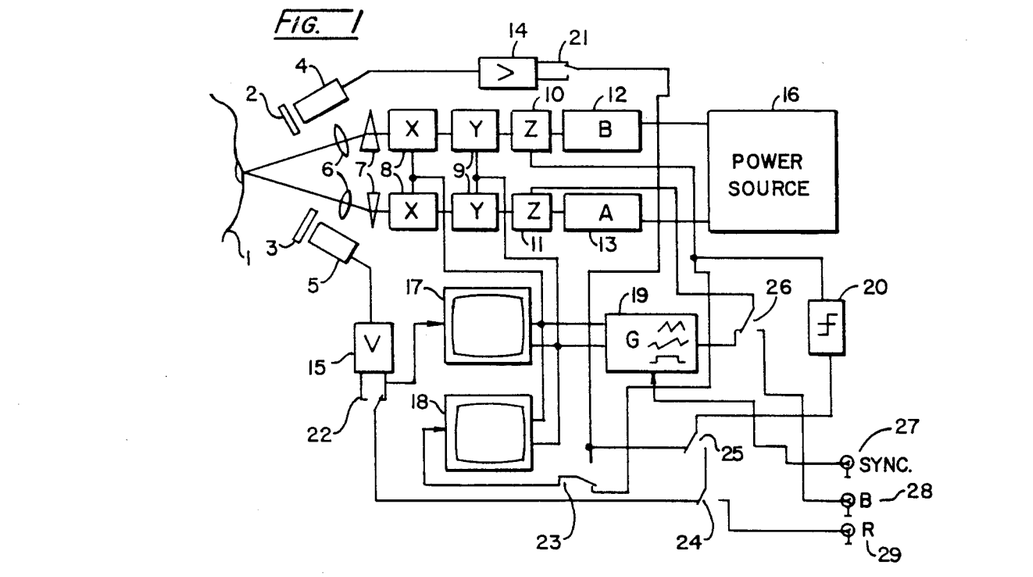
FIG. 1: A schematic drawing of a typical two laser analysis, scanner and treatment apparatus including visualization of the procedure and automatic control of both analysis and treatment laser.

FIG. 1 shows a general schematic diagram for a laser scanning and treating apparatus, generally useful for treating regions which are directly accessible to focused beams of light, typically region 1 in FIG. 1. The apparatus consists of photodetectors 4 and 5 (together with associated filters 2 and 3) having different functions as described below, focusing lenses 6 to bring the analysis and treatment laser beams to focus on the same point of the patient in region 1, converging prisms 7, two-coordinate deflectors 8 and 9 to perform a raster scan of both analysis and treatment beams over the target region (in order to perform such scan in full synchronization, deflectors 8 and 9 are driven by the same applied voltages in all cases, as shown in FIG. 1).

This typical apparatus also contains the probe or analysis laser, 13 ("A") and the effector or treatment laser, 12 ("B"), both laser beams delivered to the target region, 1, through modulators 10 and 11 respectively. The modulator 10 controlling the treatment beam is an essential feature of the present invention since it provides the means for automatic adjustment of the power delivered to the target by the treatment laser, 12.

Modulator 11 is included to provide the capability of modulating the output from the analysis laser, 13. In many laser treatments, the treatment laser, 12, causes significant thermal destruction ("burning") of the target region. Such burning tissue typically emits a broad spectrum of white background light, frequently including the wavelength of the analysis laser. Modulator 11 allows the intensity of laser 13 to be varied at typically a fixed frequency. Frequency-filtered detection (similar in principle to am radio reception) tuned to the same frequency as modulator 11 effectively separates the analysis signal from the broad-spectrum background.

Both lasers 12 and 13 are connected to a suitable power source, 16. Both photodetectors 4 and 5 are connected to appropriate amplifiers 14 and 15 respectively. Each amplifier is connected to the external circuit by means of a commutator 21 and 22 respectively, allowing either the direct or inverted output from the amplifier to be delivered to the circuit. Other commutators 23, 24, 25 and 26 are included. The apparatus also includes a threshold detection circuit, 20, a signal generator and synchronizer 19, and visual display devices 17 and 18 to assist the surgeon in manual procedures. External connections 27, 28 and 29 are also provided, the function of which will be clear in the detailed explanation of the various modes of operation of this apparatus.

This structural scheme provides flexibility of operation and allows for the stable and selective irradiation of single or plural pathological objects. This apparatus allows for the independent adjustment of both power density delivered to the target (W/cm$^2$) as well as the total delivered energy dosage of photoradiation (Joules/cm$^2$). The modulator, 10, adjusts the intensity of the treatment beam, thereby giving independent control of the power density delivered by the treatment laser beam. The scanning rate of both laser beams can be adjusted by means of the deflectors 8 and 9. The use of slower scanning rate (increased dwell time) increases the total energy dosage delivered to a particular point of the target for a constant power delivered by treatment laser 12, and constant spot size on the target. In a typical case a mirror galvanometer is used for x,y deflection. This gives typical scanning speeds of approximately 50 cm/sec. It is possible to increase the scanning speed dramatically (to speeds in excess of 1,000 meter/sec) by using an alternative embodiment of the present invention involving electron-beam pumped semiconductor lasers. This embodiment is described in more detail below.

By means of the analysis beam, the photodetectors 4 and 5, along with appropriate analyzing systems, it is possible to determine the degree of pigmentation, intensity of fluorescence and certain spectral data from each point on the target surface. Using this information, the apparatus of FIG. 1 can be used in three general ways.

The first way in which the apparatus of FIG. 1 can be used is as a combined diagnostic-therapeutic device based on the automatic determination of the target boundaries by the use of natural excitations caused by the analysis laser, 13, or with the use of photosensitizers. The use of photosensitizers may be administered superficially, directly on the target region in the manner of a conventional biological stain, or administered to the patient intravenously with expected concentration (or selective retention) by the target region, as in the case of HpD cancer treatments, for example.

This method is typically used for combined fluorescent diagnosis and photodynamic therapy of malignant and benign tumors on the skin or mucosa surfaces after photosensitizer injection. Another possible use of this apparatus involves coating the undestroyed skin or mucosa having tumor areas lying beneath, with fluorescing (but not singlet oxygen generating) dyes, followed by laser phototreatment. Another use would be in the treatment of areas on nonhealing and suppurative wounds, ulcers, skin which has been destroyed, dispigmented, hyperhaired, tattooed or inflamed, reflexogenic zones, acupuncture points, etc.

To use the apparatus of FIG. 1 in this manner, the horizontal x-deflectors, 8, the vertical y-deflectors, 9, and the visualization devices (typically video displays), 17 and 18, are connected to the signal generator-synchronizer, 19. The deflectors 8 and 9 then scan the beams of the analysis and treatment lasers 13 and 12. The optical systems 6 and 7 cause focusing of both beams on the same point on the surface of target, 1. The x- and y-deflectors 8 and 9 thus provide for a raster scan of the entire region (or some other convenient scan pattern by different choice of scanning signals produced by 19).

To perform combined therapeutic and diagnostic functions, the apparatus is typically employed as follows: The analysis laser is chosen (or wavelength-adjusted in the case of tunable lasers such as dye lasers, electron-beam pumped semiconductor lasers, free electron, or wavelength-selected for the case of multiband emissions) to excite fluorescence from the photosensitizer (if one is used) or from the specific tissue to be located. It is frequently necessary to distinguish this fluorescence from the broad-spectrum background (i.e. emitted by burning tissue. To accomplish this, modulator 11 is typically connected to the signal generator 19 by means of commutator 26. The excited fluorescence is detected by photodetector 4, typically supplied with a suitable optical filter, 2, to filter out unwanted wavelengths. Following amplification of the signal by amplifier 14, the signal goes to threshold device, 20. Threshold device 20 rejects signals below an appropriate small threshold noise signal, separating the detected signal from background. The signal from threshold device 20 is sent to modulator 10 of the treatment laser to increase the power delivered to the target by the treatment laser whenever is detected fluorescence indicates larger amounts of photosensitizer. The signal is also typically sent to display 18 for viewing by the surgeon. By such a procedure the beam of the treatment laser, 12 is modulated in direct proportion to the fluorescence intensity detected in each point of the scanned region. This includes both regions of high photosensitizer concentration (typically indicating that disease is present) as well as normal regions in which the treatment laser would be effectively switched off. Thus, efficient treatment of the entire region can be obtained automatically without the surgeon having to make estimates of required dosages and manually skipping over healthy tissues.

It is also very useful for the surgeon to be able to monitor the treatment in process. This is the function of detector 5 and display 17. Photodetector 5 is supplied with appropriate optical filters, 3, such that it receives the diffusely scattered light at the wavelength of the analysis laser, 13. This diffusely scattered light is detected by detector 5, amplified by amplifier 15 and delivered to display 17. Thus the surgeon sees on display 17 an image of the entire region under treatment, healthy as well as diseased, displayed in the diffusely scattered light of analysis laser, 13. On display 18 the surgeon sees the fluorescence from the photosensitizer. These two images can be superimposed electronically onto a single display (not shown in FIG. 1) giving the surgeon a single picture of both diseased and unaffected regions.

The present procedure electronically scans the entire region to be treated. Therefore, it is feasible to adjust the power delivered by the treatment laser, 12 to be rather less than required to fully destroy photosensitized regions with a single pass. This multipass feature allows the surgeon to proceed with better precision in tissue removal or destruction with no penalty to the patient in terms of increased time of the procedure.

It is often useful for the surgeon to employ this apparatus as a purely investigational or diagnostic device with the treatment laser, 12, switched off. The surgeon can then view the fluorescence and treatment area before deciding on the appropriate method of treatment (which may not use a treatment laser at all).

Figure 2:
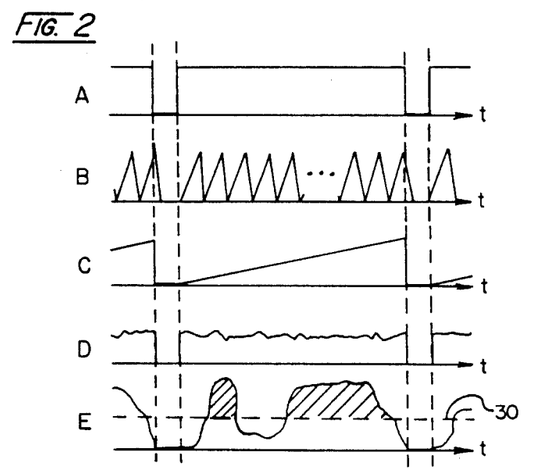
FIG. 2: Typical voltage signals that would be employed in the use of the apparatus of FIG. 1, including typical detected signals as would be obtained in use of the apparatus of FIG. 1.

FIG. 2 shows typical signals (voltage vs time) that would be employed in the apparatus of FIG. 1. FIG. 2a is the modulation of the analysis laser 13, showing that it is typically convenient to have laser 13 switched off (typically by means of modulator 11) during the "flyback" portion of the raster scan. FIGS. 2b and 2c show typical signals applied to the x- and y- deflectors respectively in order to produce a raster scan across the entire region 1. FIG. 2d shows a typical pattern of diffusely scattered light produced by analysis laser 13 and detected in detector 5. FIG. 2e shows a typical fluorescence signal as would be typically detected by detector 4. We illustrate in FIG. 2e a typical threshold 30. Signals in FIG. 2e above the threshold level, 30 (shaded areas) indicate the presence of photosensitizer in varying concentrations. Such areas would be treated by treatment laser 12 under control of modulator 10. By means of said modulator 10, increasing intensity of light is delivered to the target by treatment laser 12 for increasing voltage signals shown in FIG. 2e. Modulator 12 would stop the treatment beam from reaching the target when fluorescence signals do not reach threshold 30, thereby eliminating exposure of healthy tissue to the treatment laser.

A second way in which the apparatus of FIG. 1 can be used does not involve the use of fluorescent dyes. In this method of use the target boundaries are determined by absorption or reflection of natural or artificial pigments, and this information is used for automatic analysis and treatment in a manner analogous to that described above. However, there are some differences when the target region does not have fluorescent dyes present to define the areas requiring treatment. Medical applications falling into this category include tissue evaporation, coagulation, photothermal and photochemical decolorization, biostimulation, treatment of naturally pigmented (or artificially colored with nonfluorescent dyes) portwine stains, birthmarks, hemangiomas, other benign and malignant tumors, freckles, tattoos, destroyed, dispigmented, hyperhaired or inflamed areas of skin and other tissue, nonhealing, bleeding and suppurative wounds and ulcers, reflexogenic zones, acupuncture points, etc.

For use in this manner, modulator 10 of the treatment laser 12 is connected through the threshold device 20 and commutators 25 and 26 to the inverted output of amplifier 15. Thus, when the beam from analysis laser, 13 impinges upon the nonpigmented (and strongly reflecting) points on the target surface, the inverted output signal from amplifier 15 is very small. This causes the modulator 10 of the treatment laser 12 to stop delivery of the treatment beam to the patient. When the analysis beam from laser 13 impinges upon pigmented locations (with strongly absorbing but poorly reflecting properties), the inverted signal from amplifier 15 considerably increases. This in turn causes modulator 10 to deliver treatment laser beam to that particular spot of the target in direct proportion to the degree of pigmentation. Simultaneously, the surgeon has displayed on 17 and 18 images of the whole viewing area and of the pigmented areas, respectively. Comparing these images on the screens of the display devices 17, 18, allows the surgeon to control the process of treatment. If (in certain cases) the treatment requires irradiation of pigmented areas in inverse proportion to the degree of pigmentation, this is simply accomplished by switching commutator 22 to the opposite position from that shown in FIG. 1.

A third way in which the apparatus of FIG. 1 may be used is under full external control of analysis and treatment functions from another control device (for example, external computers, thermovision, radioactive tracer information, ultrasound, and other medical imaging methods, as well as manual detectors, etc.). For this case, we show in FIG. 1 one convenient way for connecting modulators 11 and 10 by means of commutators 24, 25 and 26 to external signal plugs, 28 and 29. External plug 27 is shown as an illustration of controlling the generator-synchronizer, 19 by an external agency.

We now describe several typical devices which can be used for the schematic components as well as certain modifications which simplify the operation of the equipment in cases where they may be employed.

Figure 3:
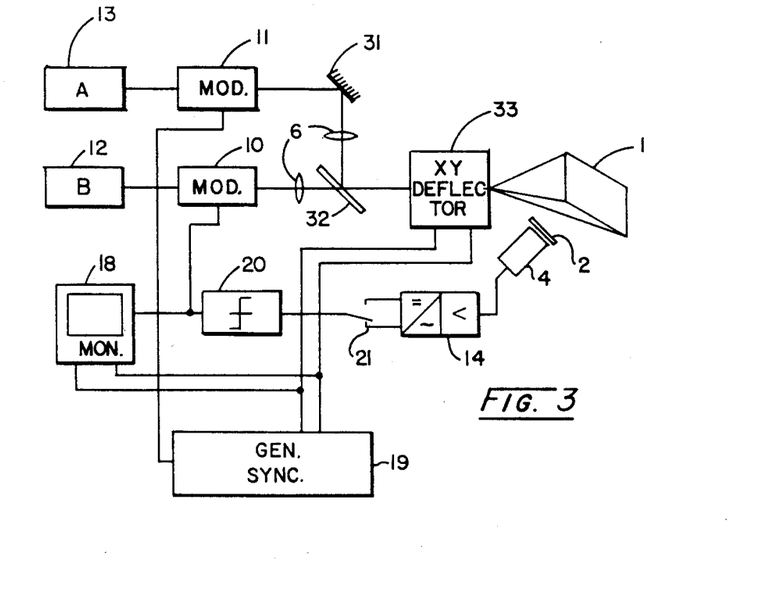
FIG. 3: A schematic drawing of a typical two laser scanning and detection apparatus in which the two laser beams are combined into a single analysis/treatment beam, including feedback and operator visualization of the process.

FIG. 3 illustrates a useful technique for combining the analysis laser beam with that of the treatment laser to require only a single x-y deflector. FIG. 3 shows the analysis laser as 13 with its associated modulator 11. This could be a low power argon ion laser, for example, operating at 488 nm. The treatment laser, could be, typically, a carbon-dioxide laser emitting at 10,600 nm, or a higher power argon ion laser typically emitting at 514 nm. In this example, the analysis laser beam emitted by the analysis laser, 13 is reflected from a totally reflective mirror, 31, focusing lens 6 and dichroic mirror 32 for combination of both analysis beam and treatment beam into a single partially coherent laser beam which can be manipulated typically by a single x-y deflector, 33. (In some cases both laser beams cannot be deflected in exactly the same way by a given deflector. In such cases, this technique cannot be employed. But even for the case of a carbon-dioxide laser, copper mirrors effectively reflect both 10,600 nm and most other wavelengths of medical interest.)

The operation of the apparatus shown in FIG. 3 is very much like that of the apparatus of FIG. 1. FIG. 3 shows only a single detector, 4 with its associated wavelength filter, 2. Generalizations of the single-beam apparatus of FIG. 3 to use both fluorescence detection as well as diffuse detection are straight forward.

In typical operation, laser 13 is modulated through modulator 11 receiving a signal from signal-generator/-synchronizer, 19. The resulting analysis beam is combined with the treatment beam by means of typically, a dichroic mirror 32. Scanning in unison is accomplished by deflector 33. Diffusely light scattered from target, 1 is filtered to remove unwanted background by optical filter, 2, detected by photodetector 4 and amplified by amplifier 14. The output from amplifier 14 (or inverted output to decrease treatment laser power in response to increasing signal), is sent to threshold device 20 and then to modulator 10 to control the output of treatment laser 12. As discussed above, the signal may also be displayed for observation by the surgeon on display device ("monitor"), 18.

Figure 4:
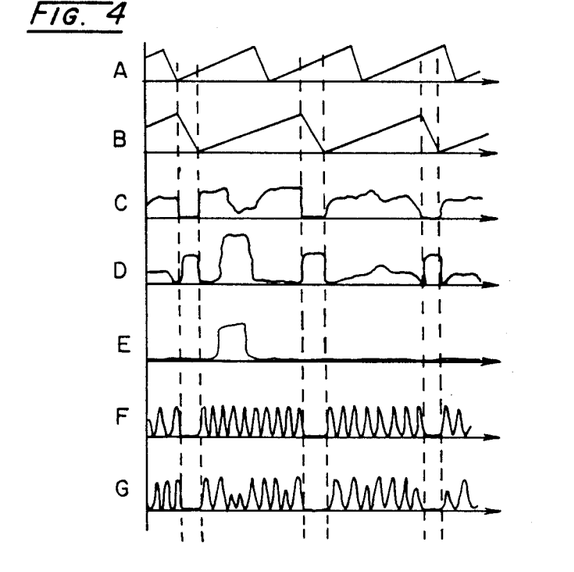
FIG. 4: Typical voltage signals that would be employed in the use of the apparatus of FIG. 3, including typical detected signals as would be obtained in use of the apparatus of FIG. 3.

Typical signals involved in the functioning of the apparatus of FIG. 3 are shown in FIG. 4. FIG. 4a and 4b show typical signals for the vertical and horizontal scanning respectively. FIG. 4c shows a typical example of the amplified and detected signal of the photodetector 4. FIG. 4d shows a typical example of an inverted and amplified signal produced by amplifier 14 following detection by detector 4. FIG. 4e shows a typical output signal from the threshold device indicating, in this example, a single continuous region to be treated by the treatment laser. FIG. 4f shows a typical high frequency modulating signal and FIG. 4g shows a typical output from the photodetector.

In typical operation the analysis laser, 13 is modulated by means of a high frequency signal, FIG. 4f by using power modulator 11 connected to signal generator, 19. The combined analysis and treatment beams are scanned over the surface of the target area, 1, by means of x-y deflector 33. Deflector 33 is controlled by the signals shown in FIG. 4a and 4b. The diffusely reflected light from the target produced by the analysis beam is received by the photodetector 4, filtered by 2 to receive only light having the wavelength of the analysis laser, 13, and the frequency of modulator 11. This signal is amplified by 14, processed at threshold device 20 and sent simultaneously to the power modulator of the treatment laser, 10 and to the input of the visual display 18. When the analysis laser contacts any point of non-pigmented, strongly reflecting, intact tissue areas, the signal is high at the output of the photodetector 4 and low at the inverted output of amplifier 14. Thus, this signal is blocked by threshold device 20 and modulator 10 prevents treatment beam from reaching the target. When the analysis beam impinges upon a pigmented area, the reflected light and the signal produced by the photodetector, 4, both decrease. This leads to an increase in the inverted power output from amplifier 14, passing through the threshold device 20 to allow proportionate intensity of treatment laser light to reach the target. At the same time, the image of the region under treatment is displayed on 18. By means of commutator 21, the apparatus shown in FIG. 3 can be used to treat regions in which treatment laser power must be directly proportional (in contrast to inversely proportional) to reflected light intensity.

It is also possible by means of an apparatus as disclosed in FIG. 3 to use a single laser having multiline emissions as both an analysis and treatment laser, taking care to separate the laser output into discrete lines and adjusting power levels as required.

A particularly useful class of lasers to use in the present set of applications is electron-beam pumped semiconductor lasers, as referenced above in a typical manifestation in the patent of Packard, for example. Such lasers are available in a variety of wavelengths, thus allowing considerable flexibility in the choice of analysis and treatment wavelengths. Also, semiconductor lasers of this type provide their own built-in scanning device by electrostatic deflection of the pumping electron beam across the face of the semiconductor, much like ordinary cathode ray tubes. This permits extremely rapid scanning rates, approximately 1000 meters/sec.

Figure 5:
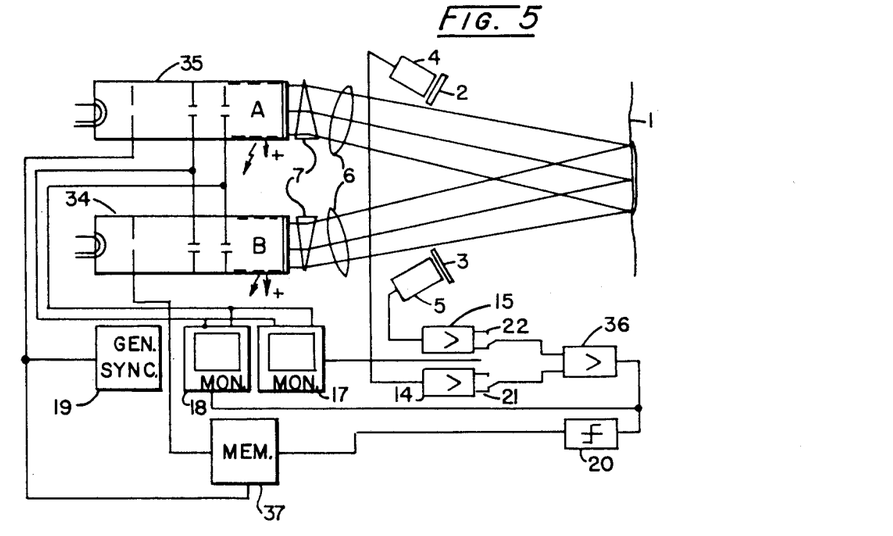
FIG. 5: A schematic drawing of a typical two laser scanning and detection apparatus as it would typically be employed with electron-beam pumped semiconductor lasers.

FIG. 5 shows a typical modification of FIG. 1 using semiconductor lasers. Analysis laser 35 and treatment laser 34 are directed to target region 1 through focusing lenses 6 and converging prisms 7. Note the absence of deflectors or modulators as these functions are readily performed by the internal electrostatic deflectors and intensity controls within each laser, 34 and 35. In analogy with the apparatus of FIG. 1, we employ photodetectors 4 and 5, filters for isolation of fluorescence, 2, and reflected light, 3, generator-synchronizer 19, wideband amplifiers with paraphase outputs, 15 and 14, differential amplifier 36, threshold device 20, digital sequence memory unit 37, TV monitors 18 and 17.

Figure 6:
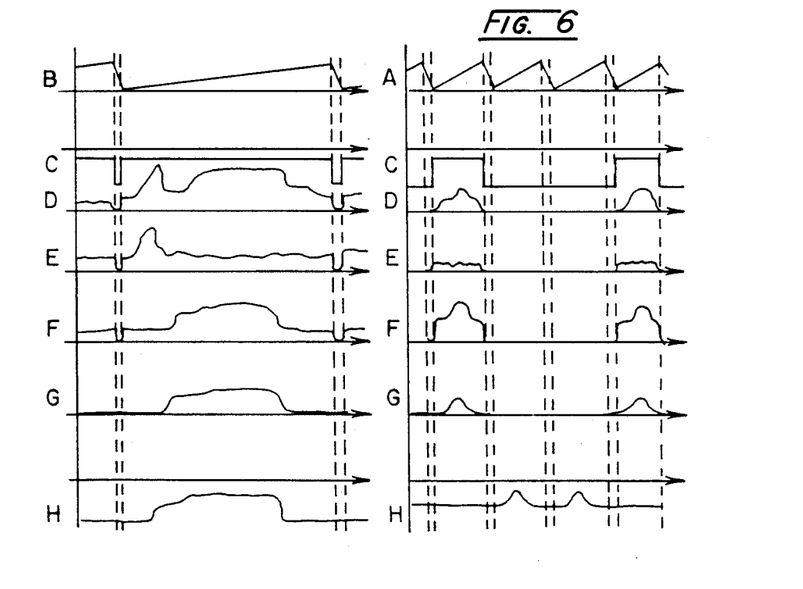
FIG. 6: Typical voltage signals that would be employed in the use of the apparatus of FIG. 5, including typical detected signals as would be obtained in use of the apparatus of FIG. 5.

FIG. 6 shows the oscillograms of the signals occurring at characteristic points of this laser scanning apparatus in typical operation. FIG. 6a shows a typical signal for the vertical (y) deflection. FIG. 6b shows a typical signal for the horizontal (x) deflection. FIG. 6c shows a typical switch-on (trigger) signal for the analysis laser. FIG. 6d shows a typical signal of the photodetector, 4 (the signal due to typical fluorescence). FIG. 6e shows a typical signal from the photodetector 5 (signal due to light reflection). FIG. 6f shows a typical output signal from the differential amplifier 36. FIG. 6g shows a typical output signal from threshold device 20. FIG. 6h shows a typical signal used to modulate the treatment laser, 34.

This typical apparatus operates as follows: The generator 19 generates the signals for line and sequence deflection of the electron beams as well as the trigger signal turning on the analysis laser, 35, which is typically a factor of 4,8,16,32, ... 256 less than the vertical deflection frequency. The beam of analysis laser 35 passes through the converging prism 7 and lens 6, reaching the target.

Excited fluorescent and reflected light beams are received by photodetectors 4 and 5 after passing through interferential light filters 2 and 3 respectively. The photodetector signals are amplified by the wide band amplifiers 15 and 14 having paraphase outputs. The reflected signal (FIG. 6e) is subtracted from the fluorescence signal (FIG. 6d) by means of the differential amplifier, 36, avoiding thereby a spurious signal from the surface of irradiated biological tissues.

The differential signal (FIG. 6f) is isolated from the background signals (FIG. 6g) by means of the threshold device 20, and sent to the digital sequence memory unit, 37, for storage and reuse during subsequent sequences. This modulation signal, FIG. 6h, is sent to the modulator of the treatment laser, 34, the output of which laser is directed, along with that of the analysis laser, 35, by means of prisms and lenses 7 and 6 respectively to the fluorescing points and areas of the region to be treated, in such intensity and duration as required for treatment without overexposure.

The signal of the reflected analysis laser beam (FIG. 6e) is sent to the TV monitor 17, while the differential signal (FIG. 6f) is sent to the TV monitor 18 for imaging of the whole irradiated surface and its fluorescing areas, respectively. The analysis and treatment laser beams are typically deflected at the usual TV standard rates (625 lines in the sequence and 25 sequences per second). For the typical case of 100×100 mm raster dimensions on the scanning surface, the speed of deflection is approximately 2000 meters/sec. At this high rate of scanning, the treatment laser beam (even using 5–10 W power and focused to a spot of 0.1 mm) does not produce significant heating of the biological tissue.

The detection of fluorescence signals having considerably smaller frequency than that of the sequencing signals (and the utilization of the digital sequence memory unit) enables the surgeon to perform multiple repetitions of the same treatment sequence in response to a single analysis scan. This can markedly reduce the (undesirable) irradiation of healthy tissue.

What is claimed is:

1. An apparatus for concurrent laser analysis and laser treatment of a two-dimensional surface comprising:
   (a) a first laser, emitting a first beam of laser light having a wavelength and power sufficient to cause characteristic fluorescence when said first beam is directed upon the surface of a target requiring treatment;
   (b) a second laser, emitting a second beam of laser light having a wavelength and power sufficient, when directed upon said target surface, to cause desired alterations in the properties of said target;
   (c) a first means for modulating the intensity of said first laser beam;
   (d) a second means for modulating the intensity of said second laser beam;
   (e) a first and a second means for focusing said first laser beam and said second laser beam, respectively, onto the same point of said target surface;

(f) a means for detecting and measuring the intensity of characteristic fluorescence emitted by said target when struck by said first laser beam;

(g) a means for regulating the intensity of said second laser beam in accordance with the measured fluorescence caused by said first laser beam;

(h) first and second two-coordinate optical scanners arranged so as to scan simultaneously said first laser beam and said second laser beam, respectively, over the same points on the surface of said target;

(i) a signal generator providing concurrent scan and trigger pulses for the control of said first and second optical scanners.

2. An apparatus as in claim (1) wherein said intensity regulating means comprises optical filtering means and feedback control circuits automatically controlling the intensity of said second laser beam by means of adjustments to said second modulator.

3. An apparatus as in claim (1) further comprising:
(a) a means for detecting the light from said first laser beam which is diffusely reflected from said target;
(b) a means to display said diffusely reflected light for visualization by an operator, creating thereby an image of said target area under treatment.

4. An apparatus as in claim (1) wherein said first and second lasers comprise semiconductor lasers pumped by electron beams, and wherein said first and second optical scanners comprise electrostatic deflecting means for deflecting said electron beams as an integral part of said lasers.

5. An apparatus as in claim (3) further comprising:
(a) a means for the display and visualization by said operator said characteristic fluorescence emitted by said target;
(b) a means for said operator to control said scanning of both said first and second laser beams over said target in response to information provided said operator by said visualizations means and said measured fluorescence intensity.

6. An apparatus as in claim (1) further comprising a means for joining said first laser beam and said second laser beam into a single beam of partially coherent light having a common direction of travel.

7. An apparatus as in claim (6) further comprising a single two-dimensional optical scanner positioned so as to scan said single joined beam over said target surface.

8. An apparatus as in claim (1) further comprising a narrowband optical filter transmitting at the wavelength of said first laser beam and positioned to filter said fluorescence from said first laser beam in reaching said detector thereof, and wherein said detector of said fluorescence from said first laser beam comprises a rectifying detector adjusted to rectify and detect at said modulation frequency of said first laser beam.

* * * * *